US012224048B2

(12) United States Patent
Daniels et al.

(10) Patent No.: US 12,224,048 B2
(45) Date of Patent: Feb. 11, 2025

(54) SPUTUM IMAGE PROCESSING ASSEMBLY AND SYSTEM, METHOD OF PROCESSING SPUTUM CONTAINED IN A SPUTUM SAMPLE CONTAINER, AND METHOD OF PROCESSING A PLURALITY OF SPUTUM SAMPLES OVER TIME

(71) Applicant: Zig Therapeutics, Inc., Carmel, IN (US)

(72) Inventors: Vicki L. Daniels, Carmel, IN (US); Joseph C. Steven, New Berlin, WI (US)

(73) Assignee: Zig Therapeutics, Inc., Carmel, IN (US)

( * ) Notice: Subject to any disclaimer, the term of this patent is extended or adjusted under 35 U.S.C. 154(b) by 0 days.

(21) Appl. No.: 18/122,035

(22) Filed: Mar. 15, 2023

(65) Prior Publication Data

US 2023/0298716 A1  Sep. 21, 2023

Related U.S. Application Data

(60) Provisional application No. 63/320,273, filed on Mar. 16, 2022.

(51) Int. Cl.
*G16H 15/00* (2018.01)
*G01N 21/17* (2006.01)
(Continued)

(52) U.S. Cl.
CPC ............ *G16H 15/00* (2018.01); *G01N 21/17* (2013.01); *G06T 7/10* (2017.01); *G06T 7/90* (2017.01);
(Continued)

(58) Field of Classification Search
CPC ................ G16H 15/00; G01N 21/17; G01N 2021/1765; G06V 10/764; G06V 10/44;
(Continued)

(56) References Cited

U.S. PATENT DOCUMENTS

2017/0315110 A1  11/2017  Chou
2020/0264167 A1   8/2020  Chen
(Continued)

FOREIGN PATENT DOCUMENTS

| WO | 2011121462 A1 | 10/2011 |
| WO | 2021202264 A1 | 10/2021 |
| WO | 2023177751 A2 |  9/2023 |

OTHER PUBLICATIONS

Swazoo Claybon III, "Automated Fluorescence Microscopy Determination of Mycobacterium Tuberculosis Count via Vessel Filtering", MS Thesis, Pub. 2017 (Year: 2017).*
(Continued)

*Primary Examiner* — Mekonen T Bekele
(74) *Attorney, Agent, or Firm* — Boardman & Clark LLP

(57) ABSTRACT

A sputum image processing assembly for processing sputum in a sputum sample container, and method of processing an image of the sputum. The assembly includes a light source to illuminate the sputum, a light sensor to acquire a reflected light from the illuminated sputum, a light enclosure to limit a light between the light source and the light sensor, and an image processor module to generate an image of the sputum with the acquired light. Further disclosed is a method of processing a plurality of sputum samples over time. The method includes acquiring a first sputum image of a first sputum sample, analyzing the first sputum image to determine first color information, acquiring a second sputum image of a second sputum sample, analyzing the second sputum image to determine second color information, and creating a time-based sputum report based on the first color information and the second color information.

20 Claims, 22 Drawing Sheets

(51) Int. Cl.
  *G06T 7/10* (2017.01)
  *G06T 7/90* (2017.01)
  *G06V 10/762* (2022.01)
  *G06V 10/764* (2022.01)

(52) U.S. Cl.
  CPC .......... *G06V 10/762* (2022.01); *G06V 10/764* (2022.01); *G01N 2021/1765* (2013.01); *G06T 2207/10024* (2013.01); *G06T 2207/20132* (2013.01)

(58) Field of Classification Search
  CPC ................ G06V 20/698; G06V 10/762; G06T 2207/10024; G06T 2207/20132; G06T 7/10; G06T 7/90; G06F 18/23213
  See application file for complete search history.

(56) References Cited

U.S. PATENT DOCUMENTS

2021/0132035 A1   5/2021   Adelman
2021/0373008 A1*  12/2021  Yaghoubi ......... G01N 33/54373

OTHER PUBLICATIONS

Jeannette et al., , "Automated Tuberculosis Diagnosis Using Fluorescence Images from a Mobile Microscope" Med Image Comput Comput Assist Interv. 2012, Pub. 2012. (Year: 2012).*

Fatma Taher et al., "Morphology Analysis of Sputum Color Images for Early Lung Cancer Diagnosis", pub. 2010 (Year: 2010).*

Swazoo Claybon III, "Automated Fluorescence Microscopy Determination of Mycobacterium Tuberculosis Count via Vessel Filtering", MS Thesis, Pub. 2017.

Jeannette Chang et al., "Automated Tuberculosis Diagnosis Using Fluorescence Images from a Mobile Microscope", Med image Comput Comput Assist Interv. 2012, Pub. 2012.

International Search Report and Written Opinion, PCT/US2023/015316, mailed Oct. 24, 2023, 14 pages.

Soumyabrata Banik et al., "Recent Trends in Smartphone-Based Detection for Biomedical Applications: A Review", Analytical and Bioanalytical Chemistry, Apr. 2021, vol. 413, Issue 9, pp. 2389-2406, Published online Feb. 15, 2021. doi: 10.1007/s00216-021-03184-z.

J. M. A. Daniels et. al., "Sputum Colour Reported By Patients is Not a Reliable Marker of the Presence of Bacteria in Acute Exacerbations of Chronic Obstructive Pulmonary Disease", Clinical Microbiology and Infection, Jun. 2010, vol. 16, Issue 6, pp. 583-588, Published online Jul. 20, 2009. https://doi.org/10.1111/j.1469-0691.2009.02892.x.

Ruan Spies et al., "Sputum Color as a Marker for Bacteria in Acute Exacerbations of Chronic Obstructive Pulmonary Disease: A Systematic Review and Meta-Analysis", Annals of the American Thoracic Society, May 2023, vol. 20, Issue 5, pp. 738-748, https://doi.org/10.1513/AnnalsATS.202204-319OC.

Marc Miravitlles et al., "Sputum Colour and Bacteria in Chronic Bronchitis Exacerbations: A Pooled Anaylsis", The European Respiratory Journal, Jun. 2012, vol. 39, Issue 6, pp. 1354-1360, Published online Oct. 27, 2011. doi: 10.1183/09031936.00042111.

International Preliminary Report on Patentability dated Sep. 26, 2024, received in connection with International Application No. PCT/US2023/015316.

* cited by examiner

| | GREEN OR YELLOW | BROWN | WHITE | BLACK | CLEAR | RED OR PINK |
|---|---|---|---|---|---|---|
| ALLERGIC RHINITIS | | | | | ✓ | |
| BRONCHITIS | ✓ | ✓ | ✓ | | ✓ | |
| CHRONIC OBSTRUCTIVE PULMONARY DISEASE (COPD) | | | ✓ | | | |
| CONGESTIVE HEART FAILURE | | | ✓ | | | ✓ |
| CYSTIC FIBROSIS | ✓ | ✓ | | | | |
| FUNGAL INFECTION | | | | ✓ | | |
| GASTROESOPHAGEAL REFLUX DISEASE (GERD) | | | ✓ | | | |
| LUNG ABSCESS | | ✓ | | ✓ | | ✓ |
| LUNG CANCER | | | | | | ✓ |
| PNEUMONIA | ✓ | ✓ | | | ✓ | ✓ |
| PNEUMOCONIOSIS | | ✓ | | ✓ | | |
| PULMONARY EMBOLISM | | | | | | ✓ |
| SINUSITIS | ✓ | | | | | |
| SMOKING | | | | ✓ | | |
| TUBERCULOSIS | | | | | | ✓ |

FIG. 4

|  | COORDINATES | | INSIDE CIRCLE CONTOUR | RGB COLOR SPACE | | |
|---|---|---|---|---|---|---|
| PIXEL NO. | X | Y | YES/NO | RED | GREEN | BLUE |
| 1342319 | 879 | 525 | YES | 255 | 255 | 128 |
| 1565270 | 1110 | 612 | YES | 160 | 160 | 72 |
| 1673429 | 1749 | 654 | YES | 169 | 209 | 142 |
| 2304402 | 402 | 901 | YES | 242 | 242 | 242 |
| 2171924 | 1044 | 849 | YES | 250 | 246 | 248 |
| 2325602 | 1122 | 909 | YES | 231 | 230 | 250 |
| 2549078 | 1878 | 996 | YES | 249 | 255 | 224 |
| 3139367 | 807 | 1227 | YES | 189 | 211 | 188 |
| 3447620 | 1860 | 1347 | YES | 84 | 130 | 53 |
| 4060886 | 726 | 1587 | YES | 247 | 251 | 220 |
| 4322927 | 1647 | 1689 | YES | 250 | 255 | 168 |
| 4782962 | 882 | 1869 | YES | 240 | 255 | 216 |
| 4943780 | 420 | 1932 | NO | 255 | 249 | 232 |
| 5605832 | 1992 | 2190 | NO | 252 | 248 | 250 |

FIG. 11

| PATIENT PROFILE | |
|---|---|
| PATIENT NAME | JOHNNY GONZALEZ |
| DATE OF BIRTH | 10/22/52 |
| GENDER | MALE |
| ETHNICITY | HISPANIC |
| LANGUAGES | ENGLISH, SPANISH |

| DISEASE STATUS | NORMAL |
|---|---|

| SPUTUM ANALYSIS TEST | |
|---|---|
| DATE | 3/1/22 |
| TIME | 8:34AM EST |
| LOCATION | PHOENIX, AZ 85044 |

| SPUTUM CATEGORY | PERCENT OF SPUTUM SAMPLE |
|---|---|
| MUCOID | 45% |
| CLEAR | 38% |
| FROTHY | 7% |
| MUCOPURULENT | 42% |
| LIGHT WHITE | 13% |
| SOLID WHITE | 29% |
| PURULENT | 4% |
| LIGHT YELLOW | 4% |
| MEDIUM YELLOW | 0% |
| DARK YELLOW | 0% |
| LIGHT GREEN | 0% |
| MEDIUM GREEN | 0% |
| SEVERE PURULENT | 0% |
| DARK GREEN | 0% |
| OTHER | 9% |
| RED | 0% |
| BROWN | 0% |
| GREY/BLACK | 9% |
| TOTAL | 100% |

FIG. 19

SPUTUM IMAGE PROCESSING ASSEMBLY AND SYSTEM, METHOD OF PROCESSING SPUTUM CONTAINED IN A SPUTUM SAMPLE CONTAINER, AND METHOD OF PROCESSING A PLURALITY OF SPUTUM SAMPLES OVER TIME

RELATED APPLICATION

This application claims the benefit of U.S. Patent Application No. 63/320,273, entitled "REMOTE DIAGNOSIS AND TREATMENT OF RESPIRATORY EXACERBATION USING SPUTUM ANALYSIS," filed Mar. 16, 2022, the entire content of which is incorporated herein by reference.

FIELD

This disclosure relates to automated color visioning systems. The disclosure more specifically relates to apparatuses, systems and methods to diagnosis and treat acute respiratory exacerbations by analyzing one or more sputum samples.

BACKGROUND

Sputum production is associated with many lung disease processes including chronic obstructive pulmonary disease (COPD) and asthma. Sputum is composed of mucous but may contain pus, blood, fibrin, or microorganisms such as bacteria. Sputum is produced when a person's lungs are diseased or damaged. Expectoration or sputum production is the act of coughing up and spitting out the sputum produced in the respiratory tract. It is difficult to assess the amount of sputum produced in a day, but there are many terms to describe it such as mucoid, purulent, mucopurulent, frothy, viscous, or bloodstained. Increased sputum production and changes in sputum characteristics often appear during acute flare-ups of COPD and asthma along with other symptoms such as more frequent and intense shortness of breath and coughing. These acute flare-ups or exacerbations can be triggered by viral infections, bacterial infections, or other causes such as air pollution, smoking, or changes in weather. Changes in sputum purulence are strongly correlated with markers of bronchial inflammation such as myeloperoxidase and leukocyte elastase present with the inflammatory cells. Sputum purulence has been shown to be the best predictor of sputum bacterial pathogens and mixed bacterial viral/atypical pathogens in patients with COPD exacerbations.

When individuals present with an exacerbation, one cannot verify a bacterial cause of an exacerbation without time-consuming laboratory analyses that can take several days to process. This makes it difficult to decide up front if antibiotic treatment is needed. A delay in antibiotic treatment can result in increased severity of acute exacerbation leading to hospitalization, pneumonia, or acute respiratory distress. Therefore, in clinical practice, patient-reported green or yellow sputum colors (e.g., sputum purulence) are often used to detect the presence of potentially pathogenic micro-organisms along with other symptoms such as fever and other exacerbation symptoms. However, sputum color reported by patients has been shown not to be a reliable marker of the presence of bacteria in acute exacerbations compared to color assessment by healthcare providers. This is likely due to several barriers including perceptual differences in color analysis and the difference in lighting conditions and ambient light during the color assessment analysis.

Because antibiotic overuse remains a medical concern, healthcare providers attempt to use the minimum dosing regimen needed to obtain the needed therapeutic response for a bacterial infection associated with a respiratory exacerbation.

SUMMARY

Systems and methods are disclosed for the remote diagnosis and treatment of a bacterial infection in individuals with chronic respiratory diseases experiencing acute respiratory exacerbations using automated color vision sputum analysis. In at least one embodiment, the system includes a mobile application, a sputum collection container, a hand-held mobile device with an embedded camera and light-emitting diodes, an attachment to control sample illumination, an image processing module where noise artifacts are extracted from the sputum image, a segmentation processing module that performs pixel-based color clustering from the plurality of sputum sample color features, and a classification module that places the color clusters into a sputum classification category. Healthcare providers can be notified of sputum purulence identification and receive a longitudinal analysis of the change in sputum purulence. In at least one embodiment, the method includes artificial intelligence-based color vision image methods to classify colors within the sputum sample and longitudinal sputum classification analysis to guide diagnosis and treatment of a bacterial infection with antibiotic treatment.

In one embodiment, a sputum image processing assembly is disclosed. The assembly processes sputum in a sputum sample container. The assembly comprises a light source to illuminate the sputum held by the sputum sample container with an illuminate light, a light sensor to acquire a reflected light from the illuminated sputum, a light enclosure to limit a light between the light source and the light sensor; and an image processor module to generate an image of the sputum with the acquired light. The sputum image processing assembly can be part of a sputum image processing system. The system can include a remote provider decision support in communication with the mobile electronic device. The assembly can include an edge device comprising the light source and the light sensor and/or a mobile electronic device comprising the light source and the light sensor.

In another embodiment, a method of processing sputum contained in a sputum sample container is disclosed. The method includes causing a light source to illuminate the sputum in the sputum sample container, acquiring light reflecting from the illuminated sputum, creating an image of the sputum with the acquired light, and analyzing the sputum image to determine color data for the sputum.

In yet another embodiment, a method of processing a plurality of sputum samples over time is disclosed. The method includes acquiring a first sputum image of a first sputum sample, analyzing the first sputum image to determine first color data, acquiring a second sputum image of a second sputum sample, analyzing of the second sputum image to determine second color data, and creating a time-based sputum report based on the first color data and the second color data.

These and other features and advantages of devices, systems, and methods according to this invention are described in, or are apparent from, the following detailed descriptions of various examples of embodiments, aspects, and constructions.

BRIEF DESCRIPTION OF DRAWINGS

Various examples of embodiments of systems, devices, and methods according to the invention will be described in detail with reference to the following figures.

FIG. 4 is a sputum color classification table providing example relationships between chronic diseases and acute medical conditions with colors.

FIG. 11 is a chart representing a portion of an 8-bit RGB color model conversion of a sample of pixels in the sputum image of FIGS. 9A-9D.

FIG. 19 depicts an illustration of a healthcare provider decision report generated by the automated sputum analysis system.

It should be understood that the drawings are not necessarily to scale. In certain instances, details that are not necessary to the understanding of the invention or render other details difficult to perceive may have been omitted. It should be understood, of course, that the invention is not necessarily limited to the particular embodiments illustrated herein.

Within the scope of this application, it is expressly intended that the various aspects, embodiments, examples, and alternatives set out in the preceding paragraphs, and the claims and/or the following description and drawings, and in particular the individual features thereof, may be taken independently or in any combination. That is, all embodiments and all features of any embodiment can be combined in any way and/or combination, unless such features are incompatible. The applicant reserves the right to change any originally filed claim or file any new claim accordingly, including the right to amend any originally filed claim to depend from and/or incorporate any feature of any other claim although not originally claimed in that manner.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
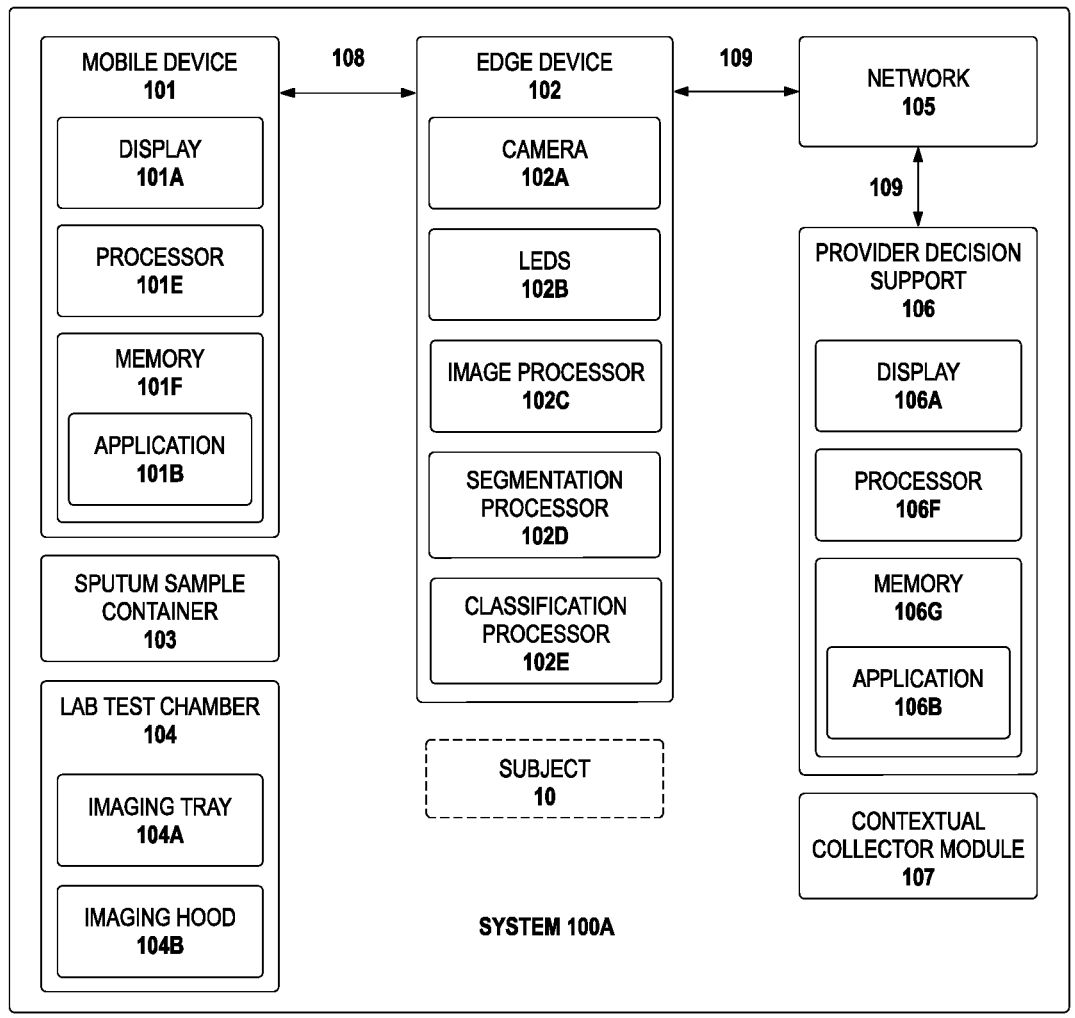
FIG. 1 is a block diagram representing a sputum color and purulence classification system.

FIG. 1 represents a system 100A for sputum color and sputum purulence classification. The system 100A includes an electronic mobile device 101 (or simply mobile device 101) having an application 101B, a display 101A, a processor 101E, and a memory 101F. The mobile device 101 can be, without limitation, a smart phone, a smart tablet, a web device, a laptop computer, and many other similar devices. In the implementations discussed herein, the mobile device 101 is a smart phone. The mobile application 101B instructs a subject 10 on sputum collection and analysis with the system 100A.

In one implementation, the subject 10 expectorates a sputum sample into a sputum sample container 103. The mobile device 101 and an edge device 102 have a communication connection 108 (for example, a Bluetooth connection) between the edge device 102 and the mobile device 101. The communication connection allows for communication and the transfer of information (e.g., data, parameters, thresholds, inputs, outputs) between the mobile device 101 and the edge device 102. The edge device 102 and or the mobile device 101 can also communicate through a network system 105 to a healthcare provider decision support system 106. Example communication 109 can include, without limitation, WiFi, 4G, and 5G.

The edge device 102 includes a housing, an embedded camera 102A, and a light source. The light source can be a plurality of light-emitting diodes (LEDs) 102B as shown in FIG. 1. However, other light sources can be used. The light-emitting diodes 102B are controlled by an image processor module 102C to acquire a high-quality image from the sputum sample. A sputum sample container 103 stores the expectorated (or induced) sputum sample. A lab test chamber 104 having an imaging tray 104A and an imaging hood 104B occludes ambient illumination during the image collection and extraction, while the light-emitting diodes 102B illuminate the sample as directed by the image processor module 102C. The mobile application 101B communicates with the image processor module 102C and prompts the subject 10 to submit the appropriate commands on the display 101A to complete a high-quality image acquisition.

The image processor module 102C pre-processes the image by extracting noise from the image and preparing the image features as input for a segmentation processor module 102D. The segmentation processor module 102D automates the segmentation of the image into pixels, classifies each pixel according to a color space model, and performs an automated color image clustering algorithm to identify clusters of similar colors in the sputum image. A classification processor module 102E classifies the sputum clusters into a sputum classification profile for a healthcare provider. The healthcare provider, through remote device 106, can inform diagnostic and treatment decisions of respiratory exacerbations with antibiotic treatment. The healthcare provider receives sputum sample analysis and alerts on a display 106A and can view serial data and antibiotic exposure through a healthcare decision support application 106B. The edge device 102, and more specifically, the image processor module 102C, the segmentation processor module 102D, and the classification processor module 102E may include physical hardware and firmware configurations, along with hardware, firmware, and software programming that can carry out the currently described methods. In at least one implementation, the edge device 102 includes a processor and memory similar to the other processor and memories described herein.

Figure 2:
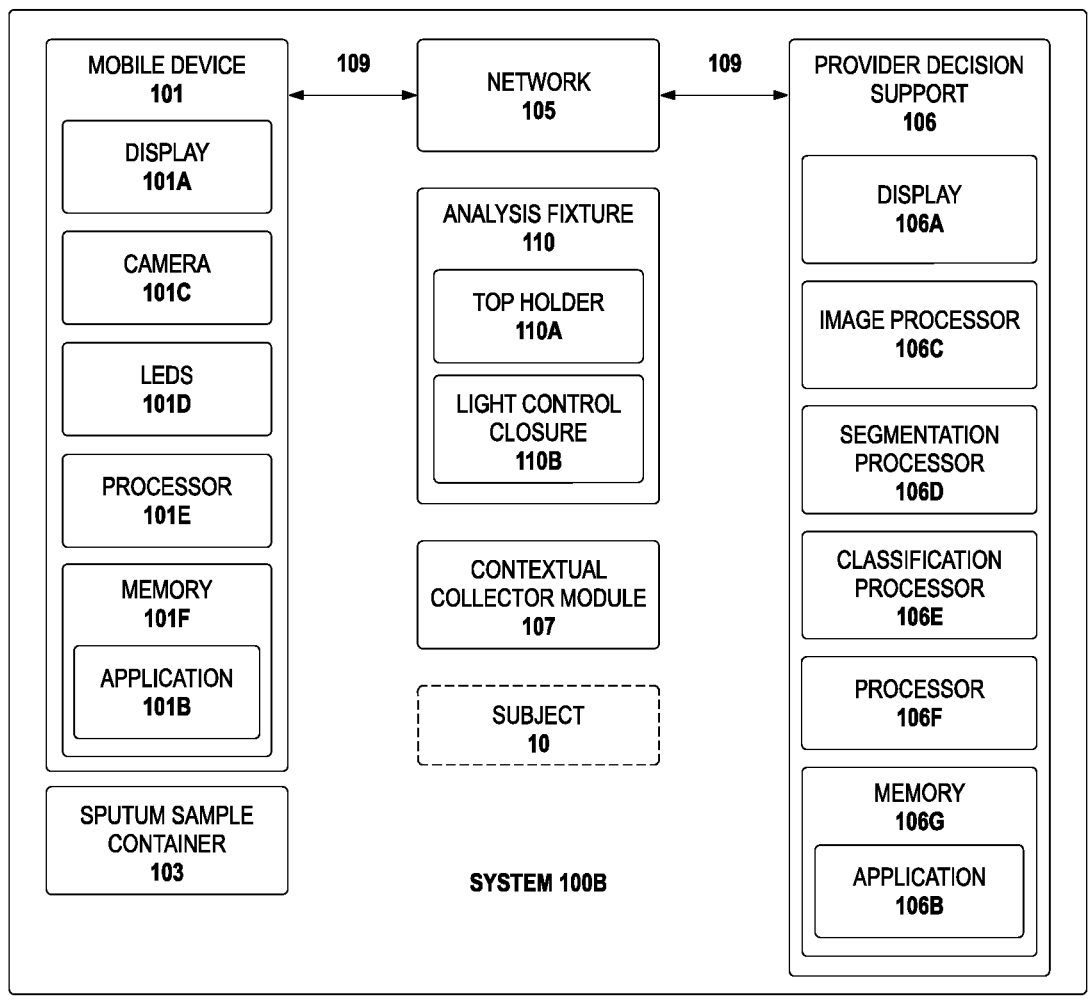
FIG. 2 is a block diagram representing a second sputum color and purulence classification system.

In another implementation as shown in FIG. 2, a second system 100B for sputum color and sputum purulence classification is disclosed. The system 100B includes a mobile device 101 having a display 101A, an application 101B, an embedded camera 101C, a light source (e.g., light-emitting diodes 101D), a processor 101E, and a memory 101F. The mobile device 101 communicates and transmits image files over the network system 105. An image processor module 106C, a segmentation processing module 106D, and a classification processing module 106E occur in the healthcare provider decision support system 106 rather than processing on a patient edge device. The image processor module 106C, the segmentation processing module 106D, and the classification processing module 106E can take the form of software instructions stored in memory 106G. The software instructions are executable by a processor 106F. It is envisioned that the software instructions, or portions thereof, can, alternatively or additionally, be stored in the memory 101F to be executed by the processor 101E.

It is contemplated that the processors and memories discussed herein may each be a single electronic device or formed from multiple devices. A processor (e.g., processor 101E, processor 106F) can include a component or group of components that are configured to execute, implement, and/or perform any of the processes or functions described herein for the device it is part of or a form of instructions to carry out such processes or cause such processes to be performed. Examples of suitable processors include a microprocessor, a microcontroller, and other circuitry that can execute software. Further examples of suitable processors include, but are not limited to, a core processor, a central processing unit (CPU), a graphical processing unit (GPU), an array processor, a vector processor, a digital signal processor (DSP), a field-programmable gate array (FPGA), a programmable logic array (PLA), an application specific integrated circuit (ASIC), math co-processors, and programmable logic circuitry. The processor can include a hardware circuit (e.g., an integrated circuit) configured to carry out instructions contained in program code. In arrangements in which there are a plurality of processors, such processors can work independently from each other, or one or more processors can work in combination with each other.

A memory (e.g., memory 101F, memory 106G) includes memory for storing one or more types of instructions, information, and/or data. The memory can include volatile and/or non-volatile memory. Examples of suitable memory include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, disks, drives, or any other suitable storage medium, or any combination thereof. The memory can be a component of the processor, can be operatively connected to the processor for use thereby, or a combination of both.

In one or more arrangements, the memory can include various instructions stored thereon. For example, the memory can store one or more modules. Modules can be or include computer-readable instructions that, when executed by the processor, cause the processor to perform the various functions disclosed for the module. While functions may be described herein for purposes of brevity, it is noted that the functions for the device are performed by the processor using the instructions stored on or included in the various modules. Some modules may be stored remotely and accessible by the processor using, for instance, various communication devices and protocols. One or more programs or modules may be stored in the memory for execution by the processor.

Before moving to other components, it should be understood by somebody skilled in the art that the electrical and electronic devices discussed herein include many additional conventional elements typically found in electrical and electronic devices. Further discussion regarding these components is not provided herein since the components are conventional and their operation is conventional.

As shown in FIGS. 1 and 2, systems 100A and 100B can further couple with a contextual data collector 107 to collect additional health data from the subject 10. The contextual data collector 107 can be part of the mobile application 101B or be a separate standalone application elsewhere (e.g., on a health provider's controlled device). The performance of systems 100A and 100B can be further improved by contextual data such as the subject's body temperature, activity measurements from accelerometers, mobile device screen use and interaction data, patient-reported systems, medication adherence sensors, messaging, and lung impairment through mobile spirometer and other breathing devices.

In some implementations, a healthcare provider or caregiver can administer a home-based or point of care sputum analysis for a subject 10. Accordingly, the use of the term "subject" 10 may apply to a provider or caregiver performing the action on behalf of the subject 10.

Figure 3:
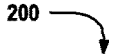
FIG. 3 is a clinical sputum color chart for assessing sputum characteristics.

FIG. 3 illustrates a clinically validated sputum color classification chart 200 to detect the presence bacterial pathogens. Colors 201 of interest often found in a sputum sample correlated with bacterial load include yellow and green. Other colors 201 may be present in a sputum sample that indicates poor air quality or severe medical conditions. Sputum is often classified according to a clinical framework 202 that defines the disease progression from normal sputum to bacterial infection. Common bacterial pathogens 203 found in a sputum sample of individuals diagnosed with a respiratory exacerbation have been shown to be correlated to sputum purulence.

Individuals with chronic diseases often produce non-clear sputum in healthy (e.g., non-exacerbation) states. Acute respiratory diseases, such as COPD, produce white sputum in a non-exacerbation state due to baseline airway inflammation or lung impairment. It is common for chronic respiratory diseases to be complemented with other chronic diseases such as allergic rhinitis, gastroesophageal reflux disease, heart failure, and sinusitis. Acute complications such as pneumonia and lung abscess often present with colored sputum. FIG. 4 illustrates a list of common chronic diseases and acute medical conditions and possible sputum color classifications 300. The patient's co-morbidities are available to the healthcare provider to better inform the interpretation of the sputum color classification.

Embodiments disclosed herein provide several advantages, either alone or in combination, and without limitation over existing methods for sputum color classification, including sputum color classification for diagnosis and treatment of acute exacerbations of respiratory disease with bacterial infection. Example advantages include: (a) more timely and accurate assessment of color features of a sputum sample to inform healthcare providers need for antibiotic treatment, (b) patient-centered automated method for home-based or point-of-care sputum color analysis rather than costly, time-consuming laboratory testing, and (c) more accurate remote monitoring of significant changes in sputum purulence to better inform the timing and dosing of antibiotic treatment.

In many individuals, a change in sputum volume and color is the first sign of an acute exacerbation. Most acute respiratory exacerbations are caused by respiratory infections, involving rhinoviruses, influenza viruses, Hemophilus influenzae, and *Streptococcus pneumoniae*. While mixed results exist, studies have demonstrated that sputum cultures identify mainly bacteria in 40% to 50% of COPD exacerbations and a causal role for viral infections in 30% to 40% of COPD exacerbations. Sputum purulence (yellow or green color) has been associated with increased odds of finding bacterial and mixed (bacterial and viral) pathogens in sputum. Sputum color change can also occur due to viral infections such as a change from clear to white.

During bacterial exacerbations new, or an increased number, of bacteria are found in sputum samples. The increase in bacteria is associated with the production of a key neutrophil chemoattractant, leukotriene B4 (LTB4) which is necessary to drive neutrophil influx. The release of LTB4 is likely dependent upon the bacterial load. As bacterial numbers rise, the neutrophils in the lung also rise, and the sputum tends to become green and be classified as purulent. Purulent sputum typically reflects neutrophil influx into the secretions. For this reason, the purulence of sputum can be used as a guide to the presence of infection. It not only reflects the likelihood of identifying bacteria but also the bacterial load and the inflammation and damaging potential of the secretions. Purulent sputum color has been validated as a good marker of bacterial involvement in acute exacerbations of chronic respiratory diseases and often guides physicians in deciding on antibiotic treatment.

When individuals with chronic respiratory disease experience worsening symptoms, healthcare providers instruct patients to assess the colors of their sputum sample at home as a marker of the presence of bacteria in an acute exacerbation. Most healthcare providers rely on the patient-reported sputum color to guide antibiotic therapy decisions to address bacterial infections related to an acute exacerbation rather than order laboratory testing. Having a color chart to assist with the assessment of sputum color can improve the accuracy of the patient's color classification compared to just asking them if their sputum has become greener. However, sputum color assessed by patients with a color chart is not a reliable marker of the presence of bacteria in acute exacerbations compared to assessments made by healthcare professionals. This suggests that having a color chart is likely to improve the objectivity of the sputum color assessment but there will still be a degree of subjectivity in the assessment. There does not appear to be any published data on the inter-or-intra-rater reliability of the color chart sputum assessment tool.

Individuals can have different perceptions of the same color and that perception can be impacted by the lighting conditions and ambient light. Unless a sputum sample can be accessed under similar lighting conditions and ambient light, it is likely that the inter-or-intra reliability of perceptual color chart sputum assessment will be low. Furthermore, human color assessment is inherently biased. The basis for human vision is the network of light sensors in human eyes. These sensors respond to different wavelengths by sending unique patterns of electrical signals to the brain. In the brain, these signals are processed into the sensation of sight—of light and of color. As a human's memory system recognizes distinct colors, then the human associates a name with the color. Distinguishing between the boundaries of sputum colors of clear to white, white to yellow, yellow to green, green to darker green, and darker green to grey/black are essential in informing a healthcare provider's decisions on antibiotic therapy. Further, early detection of color changes in sputum images over time is difficult for the human eye to discriminate particularly under different lighting conditions and ambient light.

Having a standardized system and method for classifying sputum color diminishes the potential impact of lighting conditions and ambient light on the color classification. Further, a standardized system and method for classifying sputum color diminishes lessens the potential perceptual bias that a patient may have in the interpretation of the color of the sputum sample. By having consistent, reliable sputum color classification, accurate measures of the changes in sputum purulence can be collected over time compared to a baseline sputum color profile. Early identification of sputum purulence and other acute medical conditions associated with cardiovascular co-morbidities, such as heart failure, can be achieved through the systems and methods described herein.

In some cases, the earliest sign of an acute respiratory exacerbation is changes in sputum production and color. Earlier intervention into the treatment of an acute exacerbation with oral corticosteroids and if needed, antibiotic treatment, can reduce the severity and the likelihood of a life-threatening medical event such as acute respiratory distress and pneumonia.

The current standard of care to diagnose a bacterial infection is either patient-reported sputum color assessment or laboratory sputum analysis. Laboratory testing requires a patient to produce a sputum sample in their home and to transport it to a laboratory or to produce an induced sputum sample in a laboratory. Common sputum analysis tests require two to three days to detect the growth of specific bacteria in the sputum sample. Other faster laboratory tests are more expensive and likely less accessible except at a hospital laboratory. Scheduling and/or traveling to a laboratory can be cumbersome for a patient experiencing an acute exacerbation and increases their risk of exposure to viral infections which could complicate the severity of their acute exacerbation.

A home-based or point-of-care sputum collection and analysis system has an advantage of being non-invasive and time-efficient. The home-based or point-of-care sputum collection may require only a few additional minutes of the subject's time to collect and analyze. The sample can be obtained using a mobile application on a smart phone, for example, to instruct the subject in the steps to complete the processing of the sputum sample. The automated reporting of the sputum sample to a healthcare provider enables the early identification of an acute exacerbation. Home-based sputum collection, image collection, and automated analysis enables serial collection of sputum to detect changes. Multiple collections can be more informative to a healthcare provider rather than a single laboratory sputum culture analysis. For some subjects, detecting bacterial pathogens is not the same as having an infection. Individuals with respiratory disease lungs have airway inflammation and bacteria present in their normal sputum cultures when an acute exacerbation is not present.

In one or more implementations, apparatus, system, and methods disclosed herein allow for serial sputum color analysis to detect color changes in serial sputum images over time. Serial sputum color changes can be reported to a healthcare provider to inform their decision making while also correlating color changes with other contextual factors such as patient-reported symptoms and fever. According to evidence-based standards, acute respiratory exacerbations are defined as a worsening of a patient's symptoms from the normal variations in their daily respiratory symptoms such as shortness of breath, coughing, and sputum production. By having quantitative assessments of the change in sputum color rather than patient-reported assessments, one or more of the implementations have the advantage of providing more accurate information on the worsening of respiratory diseases symptoms to a healthcare provider. Along the same lines, the healthcare provider can be better informed of the therapeutic impact of antibiotic exposure over time by requesting that the patient provide daily sputum samples to measure the change in sputum purulence and to adjust antibiotic dosing regimens to ensure a return to a patient's normal sputum baseline.

Figure 5A:
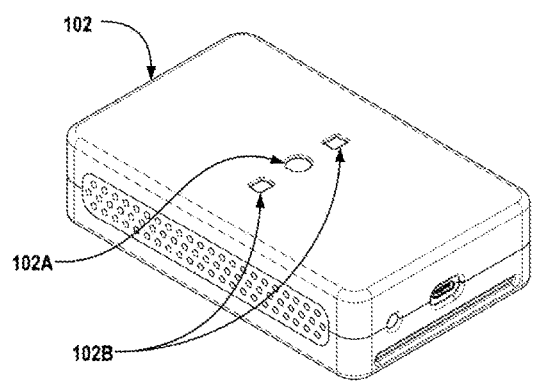
FIG. 5A is a perspective view of an edge device used in the assembly of FIG. 5.
Figure 5:
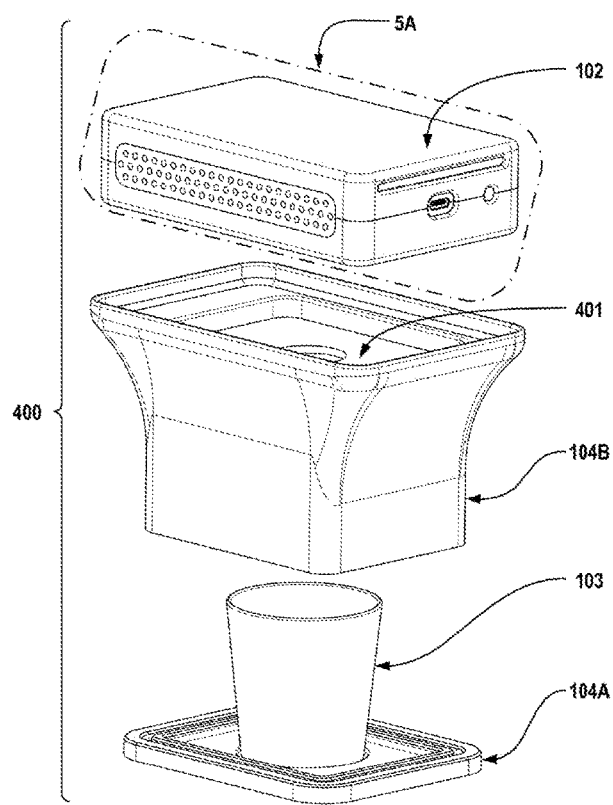
FIG. 5 is an exploded view of an assembly for obtaining a home-based or point-of-care sputum image using an edge device used in the system of FIG. 1.
Figure 6:
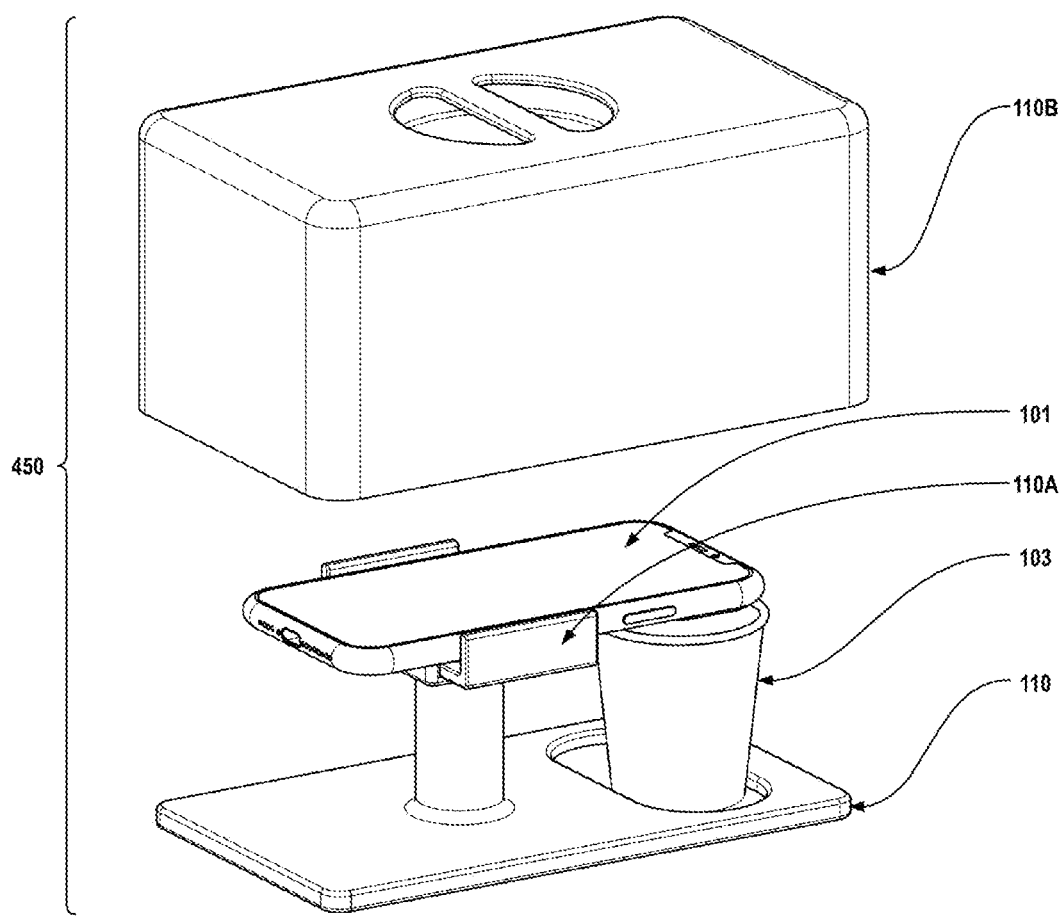
FIG. 6 is a partially exploded view of a second assembly for obtaining a home-based or point-of-care sputum image used in the system of FIG. 2.

FIGS. 5, 5A, and 6 illustrate two constructions of the components of a sputum image processor assembly 400 and 450. In the construction of FIGS. 5 and 5A, image acquisition occurs on the edge device 102 with the embedded camera 102A and the light-emitting diodes 102B. The assembly 400 also includes a lab test chamber, having an image tray 104A and an imaging hood 104B, and the sputum sample container 103. The assembly of the components and their proper placement is shown in FIG. 5 where the sputum sample container 103 is placed into the imaging tray 104A on a flat surface, the imaging hood 104B is placed over the sputum sample container 103, and the edge device 102 is placed on top of the imaging hood 104B with camera-facing inside the lab test chamber 104. In some embodiments, a light diffuser 401 is contained within the imaging hood 104B to further modify the light emitted from the light-emitting diodes 102B.

In the construction of FIG. 6, the camera 101C and light-emitting diodes 101D of the mobile device 101 replace the edge device 102. Subject 10 places the sputum sample container 103 onto the base of a sputum analysis fixture 110. The mobile device 101 is inserted into a top holder 110A of the sputum analysis fixture 110 with the camera 101C placed directly above the sputum sample container 103. Next, subject 10 places a light control closure 110B over the other components of the sputum analysis system 450.

Figure 7:
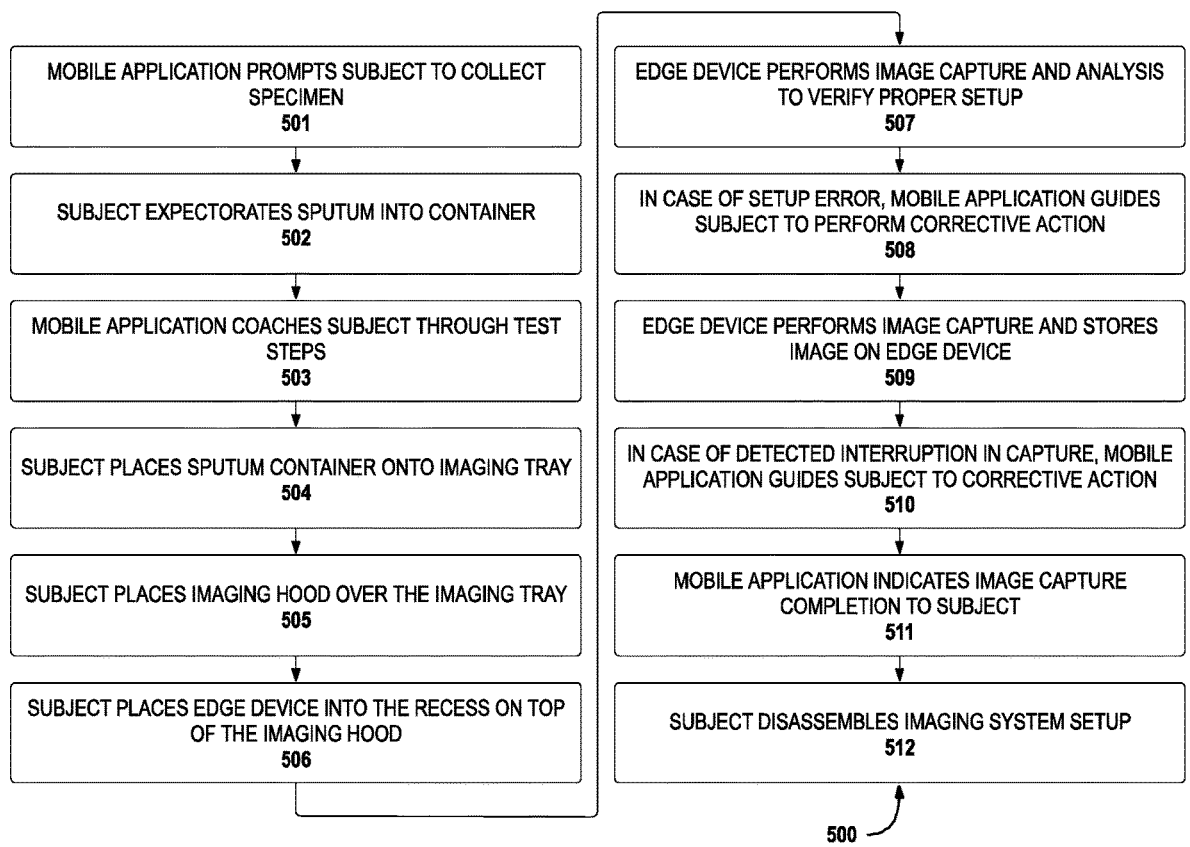
FIG. 7 is a flow chart representing a method for obtaining a sputum sample from a subject and obtaining a sputum image.
Figure 8:
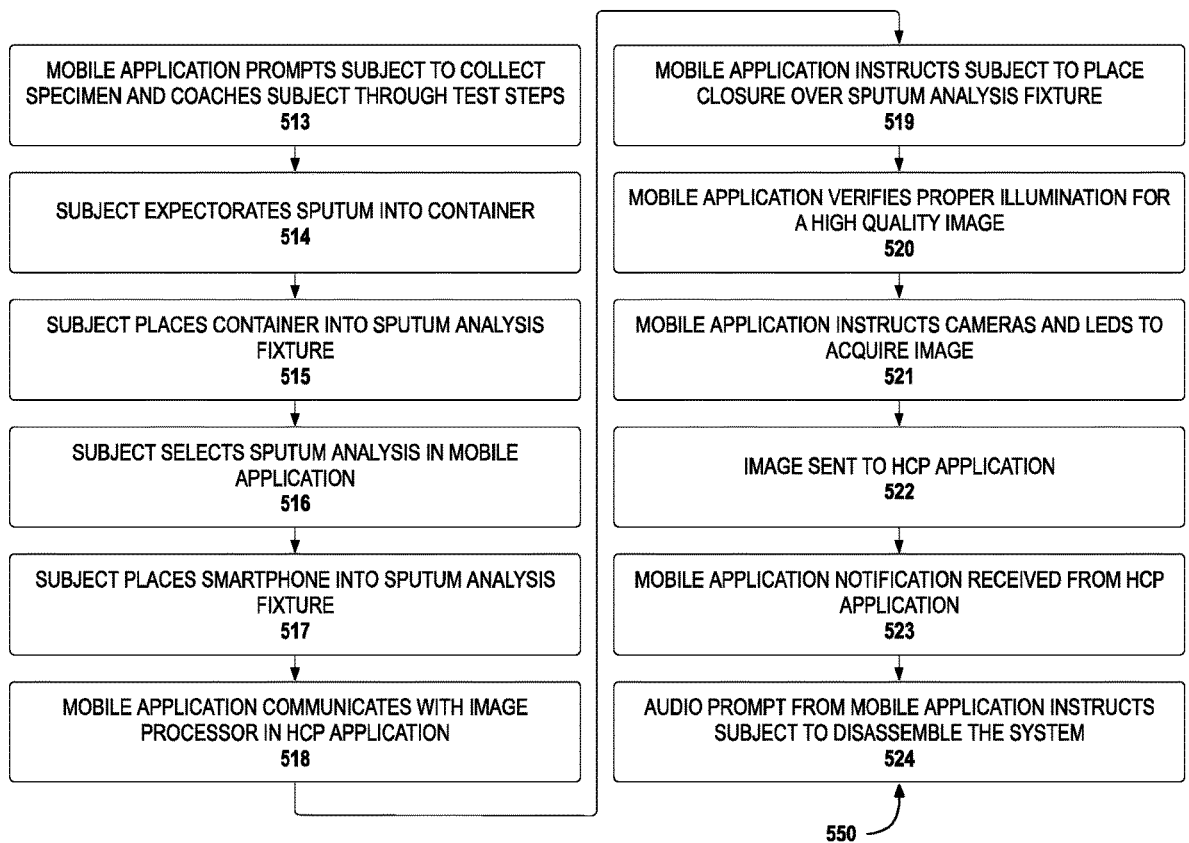
FIG. 8 is a flow chart representing a second method for obtaining a sputum sample from a subject and obtaining a sputum image.

FIGS. 7 and 8 provide process flows 500 and 550 of a subject acquiring an image of a sputum sample. First with FIG. 7, the subject 10 is prompted and coached (S501) to collect a sputum sample through the use of the mobile application 101B. Subject 10 may also elect to collect a sputum sample without prompting during periods of worsening respiratory symptoms. The mobile application 101B coaches the patient through the process of collecting (S502) the sputum sample into a sputum specimen container 103. The mobile application 101B provides (S503) the subject 10 with instructions for performing the sputum analysis test. The subject 10 then places (S504) the sputum specimen in the container 103 on the imaging tray 104A. The imaging hood 104B is then placed (S505) over the sputum sample container 103. Next, the edge device 102 with the embedded camera 102A and light-emitting diodes 102B is placed (S506) over the top of the imaging hood 104B with the camera 102A facing inside the imaging hood 104B. The edge device 102 then performs image capture and analysis (S507) to check the placement of the camera 102A facing inside the imaging hood 104B. In case of setup error, the mobile application 101B guides (S508) the subject 10 to perform corrective action. The edge device 102 then performs image capture (S509) to acquire and save the sputum image (an example of which is discussed below) on the edge device 102. In case of error, the mobile application 101B guides (S510) the subject 10 to perform corrective action. After capture, the mobile application 101B notifies (S511) subject 10 of the completion of the test. The subject 10 is instructed to disassemble (S512) the lab test chamber and to dispose or clean the sputum sample container 103.

Referring now to FIG. 8, the figure provides a process flow 550 for a mobile device 101 (e.g., smart phone) acquisition of a sputum image. The mobile application 101B prompts and coaches (S513) the subject 10 to collect the sputum sample based on a healthcare provider defined schedule or monitoring of contextual factors. The subject 10 expectorates (S514) sputum into the sample container 103. Next, the subject 10 places (S515) the container 103 flat on the sputum analysis fixture 110. To begin the sample analysis, subject 10 selects (S516) the sputum analysis option in the mobile application 101B before placing (S517) the mobile device 101 into the sputum analysis fixture 110. The mobile application 101B communicates (S518) with the image processor module 106C of the healthcare provider decision support application 106B to begin the sputum sample analysis. The mobile application 101B instructs (S519) the subject 10 to place the light control closure 110B over the sputum analysis fixture 110 to control the lighting conditions. The mobile application 101B verifies (S520) proper placement of the sputum analysis fixture 110 to allow for a high-quality image. If needed, the mobile application 101B prompts subject 10 to change the configuration of the mobile device 101 (e.g., smart phone), sputum sample container 103, fixture 110, and closure 110B to ensure proper illumination. The mobile application 101B sends (S521) signals to the camera 101C and the light-emitting diodes 101D to acquire the image and store the image on the mobile device 101. The image is then sent (S522) to the healthcare provider decision support application 106B for processing and sputum color classification. The mobile application 101B receives (S523) notification that the healthcare provider decision support application 106B has received the sputum image. An audio prompt is activated (S524) from the mobile application 101B that notifies subject 10 to remove the light control closure 110B and disassemble the assembly 110.

Figure 9A:
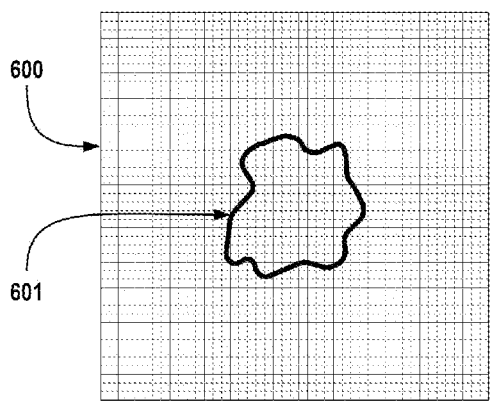
FIGS. 9A-9D illustrates of a sputum sample image collected by either FIG. 7 or FIG. 8.
Figure 9B:
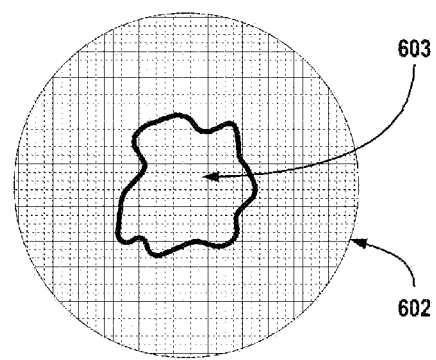
Figure 9C:
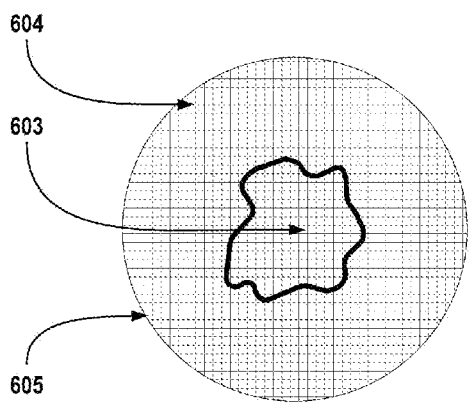
Figure 9D:
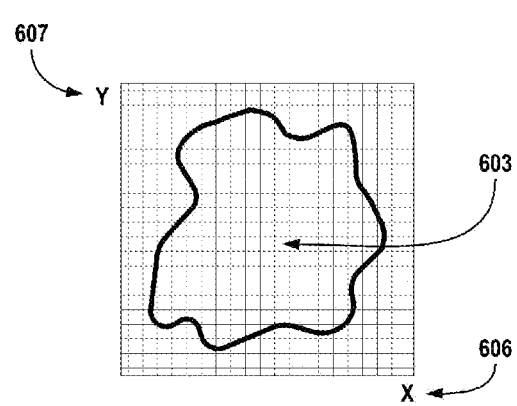

FIGS. 9A-9D provide illustrations of a sputum image captured by the process flow 500 or 550. In FIG. 9A, the unprocessed sputum image 600 is represented by pixels 603 that correspond to the subject's 10 sputum sample 601 and the sputum sample container 103 background. In FIG. 9B, the sputum image processing identifies the bottom contour 602 of the sputum sample container 103 and the sputum sample 601 relative to the bottom of the collection container. In FIG. 9C, a grid axis coordinate overlay 604 is placed over the image of the sputum sample container bottom 602 to facilitate identifying the coordinates of pixels squarely within the bottom contour 602 and to remove the partially included or rounded edge pixels 605 from processing. As further shown in FIG. 9D, the grid axis coordinate overlay 604 provides locational positioning of the pixels by identifying the x axis 606 and the y axis 607.

Figure 10:
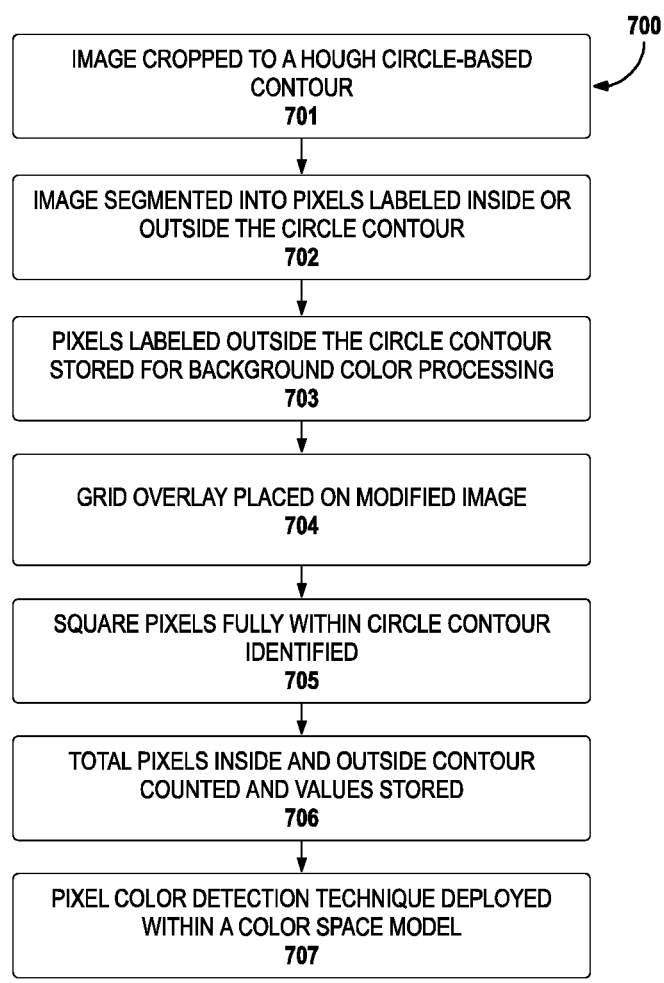
FIG. 10 is a flow chart representing image processing and segmentation of a sputum image.

FIG. 10 provides a process flow 700 for image processing and segmentation of a sputum image 600. After acquiring the image 600, the image processing module 106C performs the pre-processing steps to convert the image data into the form that allows artificial intelligence models to solve a sputum classification problem. In one implementation, the sputum image 600 is cropped (S701) to the largest Hough circle-based contour to identify the bottom of the sputum sample container 103 from the outside container wall surface areas captured by the camera. In another implementation, the image is cropped to a circle-based contour with canny edge detection. Next, image segmentation partitions (S702) the digital image into pixels 603 and labels the pixels as inside or outside the circle-based contour. The pixels located outside the circle contour and stored for further processing of the background color of the sputum collection container (S703). The modified circle sputum image 602 is considered multidimensional data and the pixels 603 are represented by multiple features including, among other things, color, volume, and spatial information. A grid overlay 604 is placed (S704) on the modified circle image 602 to extract the round-edge pixels. The remaining square pixels will be identified (S705) with x and y coordinates based on their position on the grid. The total number of pixels inside the modified circle sputum image is counted and stored as TS and the total number of pixels outside the circle-based contour is counted and stored as TO (706). The pixel spatial location coordinates allow for examination of the geometries of the sputum in the container during classification processing. Color detection techniques are deployed (S707) to identify any color in a given range using a specific color space model for each pixel with assigned x and y coordinates and for pixels outside the radius of the circle contour. In one implementation, colors in digital images are represented by the RGB model which describes colors in terms of three channels around the amount of red, green, and blue it contains. An automated color profile indicator defines the target color space for each pixel in the modified circle sputum and for the pixels outside the circle contour.

FIG. 11 illustrates the method 800 of an 8-bit RGB color model conversion of a sample of pixels in a sputum image 600 into multi-dimensional data. The sputum sample image pixels are identified with a unique number 801. For each pixel, the x axis 802 and y axis 803 coordinates are identified along with the contour location 804 and the specific RGB color model numbers 805. Other implementations of the RGB color model can be represented by a 16-bit or a 32-bit floating point for each color component. In other implementations, the color model can be represented by HSV color model with three channels: hue, saturation, and intensity value, respective of a color; Lab color model where "L" in Lab refers to the lightness of a color, the "a" represents the red-green components, and the "b" represents the blue-yellow components; the YCbCR color model, and other color space models.

Figure 12:
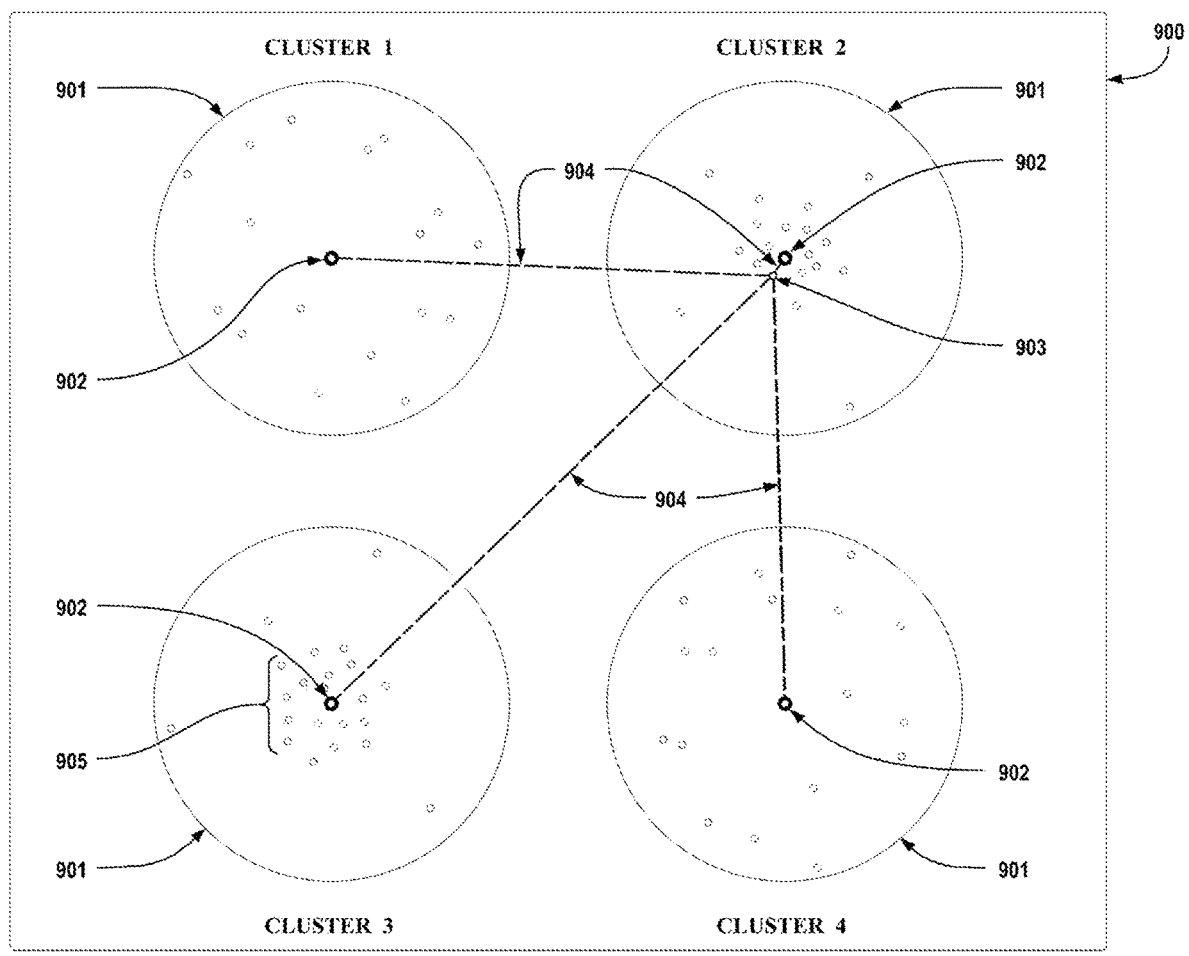
FIG. 12 are sample illustrations for color classification of pixels using a 2-dimensional k-means clustering algorithm.

FIG. 12 depicts an illustration of the method 900 for color classification of pixels using a 2-dimensional k-means clustering algorithm example. The k-means algorithm is an iterative methodology to partition the set of image pixels into "k" pre-defined clusters 901 where each pixel belongs to only one cluster. Each cluster has a unique centroid 902 defined by cluster feature set. This clustering method makes the intra-cluster pixel features as similar as possible while keeping the "k" cluster features as different as possible. Each pixel 903 is assigned to a cluster such that the squared Euclidean distance (sum of the squared distance) 904 between the pixel 903 feature set and the cluster's centroid feature set 902 is at the minimum. The less variation 905 within the clusters, the more homogeneous the pixel features within a cluster.

Figure 13:
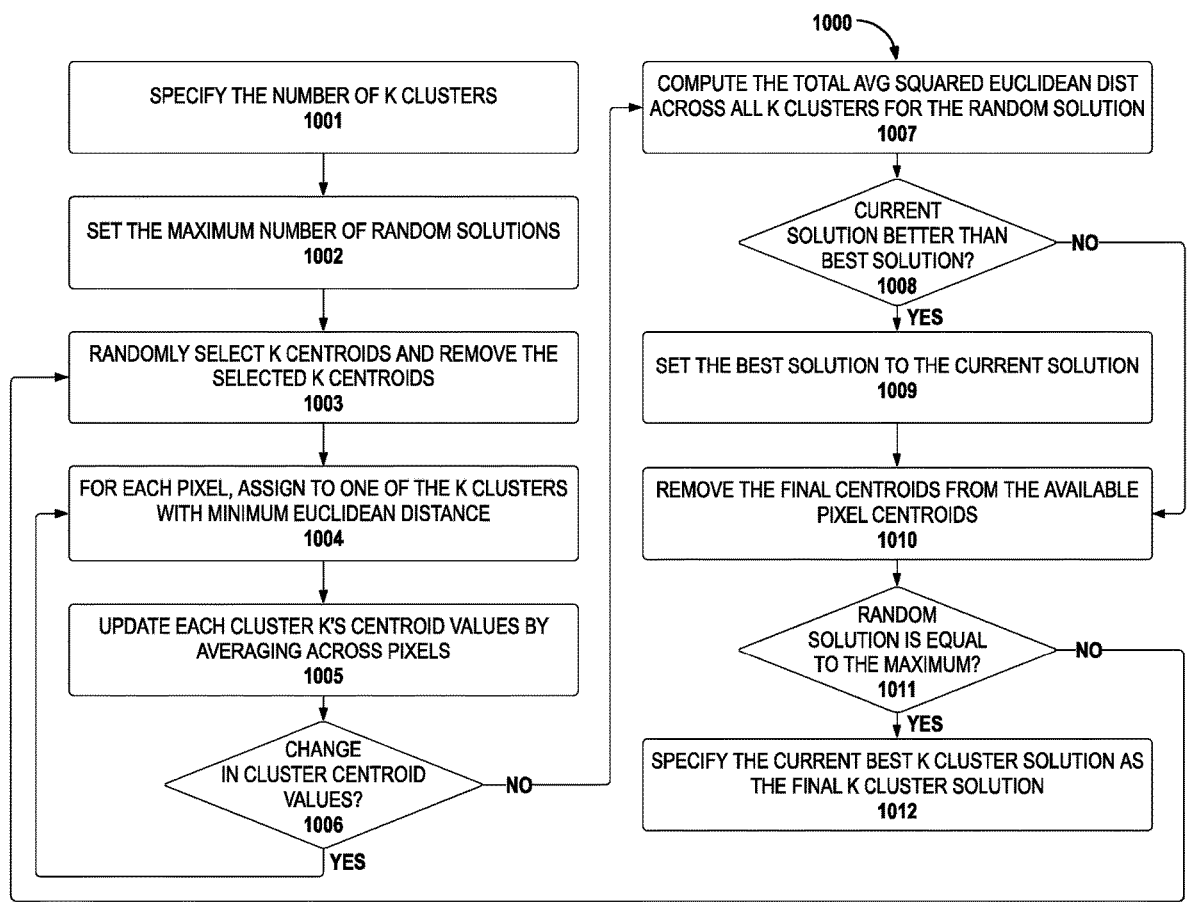
FIG. 13 is a flow chart representing a method of sputum color classification of a sputum sample.

FIG. 13 provides a process flow of the method 1000 for the sputum color classification k-means algorithm evaluates the performance of a range of pre-specified k clusters. The algorithm inputs are the number of clusters K and the pixel data set. The algorithm begins with a specified number of k centroids (S1001). The algorithm evaluates a maximum number of random starting k-centroid solutions (S1002) and identifies the best solution from different random k-centroid solutions. The algorithm randomly selects the k centroids from the available centroid pixel data set and removes these k centroids from the available centroid pixel data set (S1003). Each k centroid is defined by the associated pixel RGB values. Then, the algorithm iterates between two steps until stopping criteria for a specific random k-centroid solution are satisfied. First, the algorithm assigns a pixel to the nearest centroid based on the minimum squared Euclidean distance between the pixel's RGB features and the centroid RGB cluster features (S1004). Next, the centroids for each of the k clusters are updated to reflect the new assignment by taking the average of the squared Euclidean distance across the pixels that belong to each cluster k (S1005). Using the revised k-cluster RGB centroid, the algorithm returns to step one (S1004) and repeats the process until there is no change in centroids for the k clusters (S1006). In other implementations, the stopping criteria may be a maximum number of iterations is reached or a weighted sum of distances is minimized. When the stopping criteria are achieved (S1006), the algorithm computes the total average squared Euclidean distance of the pixel features assigned to each cluster across all k clusters for the random starting k centroid starting solution (S1007). The algorithm compares the current random solution total average squared Euclidean distance to the best solution's Euclidean distance (S1008). If the current solution is better than the best solution, the algorithm updates the current solution as the best k-cluster solution (S1009). The final centroids of the best solution are removed from the available pixel centroids (S1010). If the current random solution is equal to the maximum number of random solutions (S1011), then the k-cluster algorithm converges with the best solution as the final k-cluster solution (S1012). If not, the algorithm returns to generate another random solution by specifying a random set of k centroids (S1003).

Figure 14:
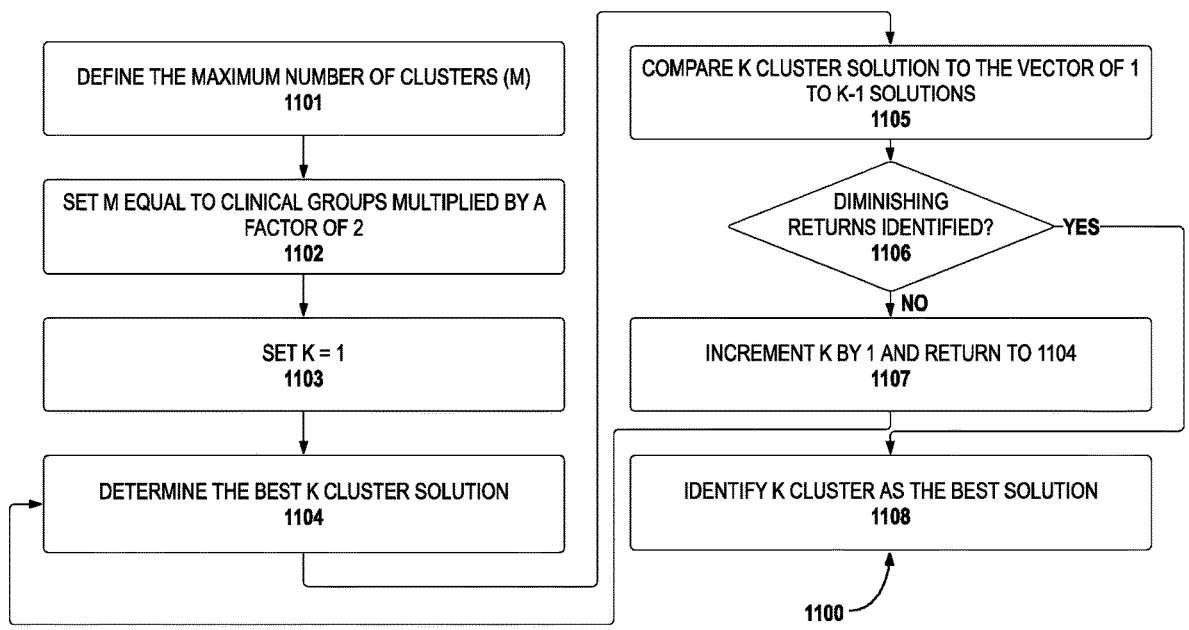
FIG. 14 is a flow chart representing a method of sputum color classification of a sputum sample.
Figure 15:
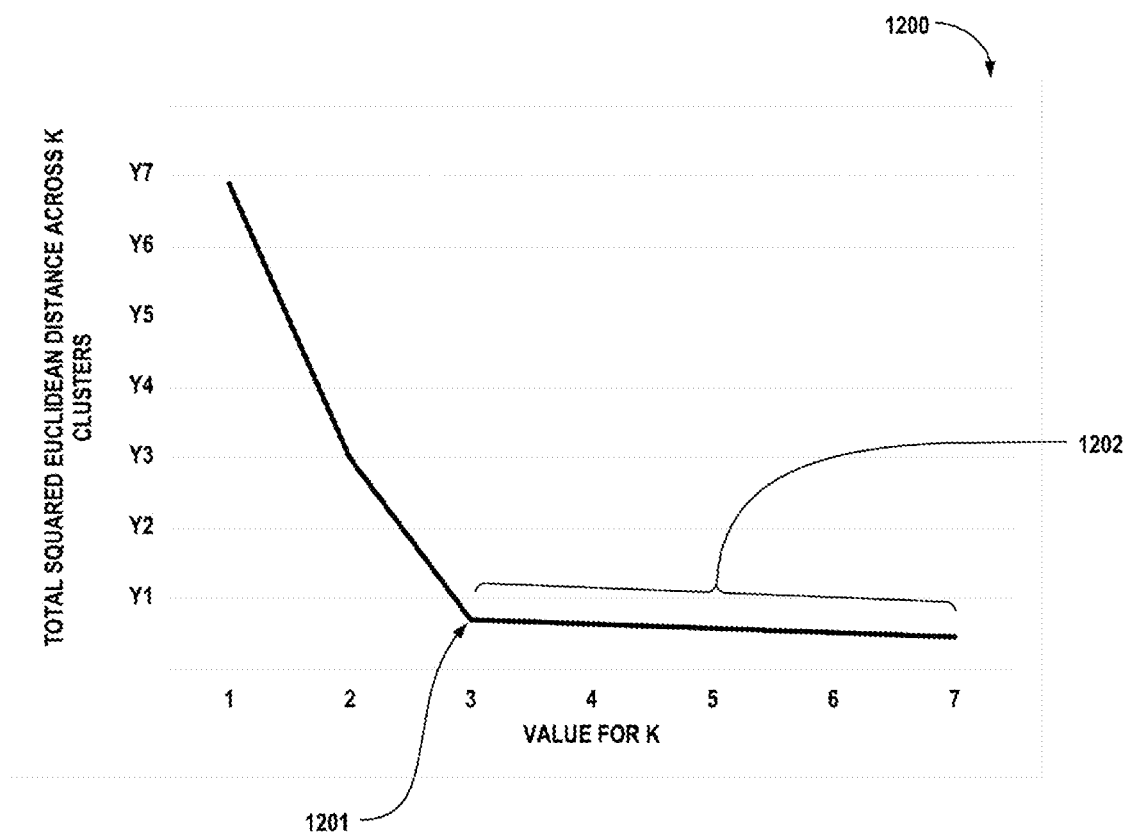
FIG. 15 is a graph showing an "elbow point" method of clustering.

In this implementation and as shown in FIG. 14, the sputum color classification k-means method 1100 evaluates the performance of a range of k clusters from 1 up to a maximum value number of clusters. The maximum value (M) is defined (S1101) to be the number of clinically relevant groups specified in clinical sputum classification framework multiplied by a factor of two (S1102). The algorithm iterates through different k cluster values beginning with the of value of 1 (S1103) until either a point of diminishing returns has been identified or M k-cluster solutions are generated. For a value of k, the best k-cluster solution is determined (S1104) from the randomly generated solutions. The algorithm compares (S1105) the k-cluster solution to the previous 1 cluster to current k–1 solutions. To identify the number of k-clusters that result in the best representation of the sputum sample, the clustering algorithm must compare results across different values of k clusters. Since increasing the number of k clusters will always improve the average squared Euclidean distance, the best solution would be k clusters equal to the number of pixels in the modified sputum sample data set which is not a pragmatic solution. The sputum analysis k-means clustering algorithm instead uses an iterative approach that increments the number of k clusters up to the point where the rate of improvement from adding an additional cluster does not improve above a pre-specified threshold rate (S1106). The best number of clusters and the best sputum analysis solution is determined (S1108) when the k value at the initial point of diminishing returns is identified. If the point of diminishing returns does not appear, the algorithm increments (S1107) by 1 and k concludes at the maximum value of M. The best k-cluster solution is identified (S1108) from the M solutions. This "elbow point" method 1200 is shown in FIG. 15 where the best value of k is when the diminishing returns of adding another k cluster 1201 does not improve over a pre-specified number of k clusters 1202.

Figure 16:
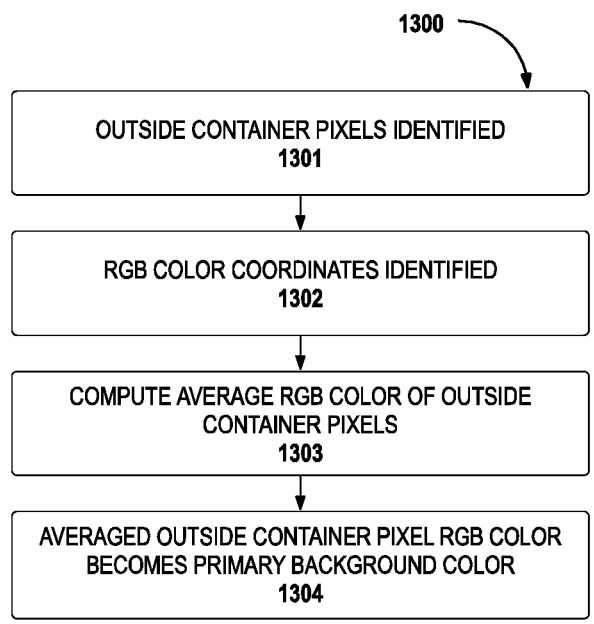
FIG. 16 is a flow chart representing a method for identifying a sputum sample container background color.

FIG. 16 provides a process flow of method 1300 for identifying the sputum sample container background color. The sputum sample container 103 background color may impact the sputum sample color classification. When the sputum sample contains clear, cloudy, white, or light color shades, the container background color may blend into the color classification. For example, clear sputum on a grey background sputum sample container could appear as a bright grey pixel color. To identify the primary background color of the sputum sample container, the outside container pixels are identified (S1301) and the associated RGB color coordinates are identified (S1302). The algorithm then computes (S1303) the average RGB colors of the outside container pixels. The averaged (S1304) outside container pixels RGB color space becomes the primary background color for the sputum sample container.

Figure 17:
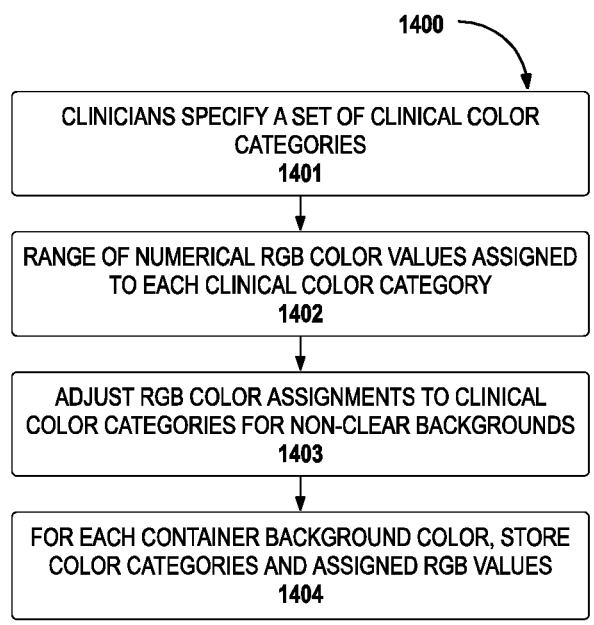
FIG. 17 is a flow chart representing a method of a clinical expert classifying a color space model into clinical sputum categories.

Referring now to FIG. 17, a process flow of the clinical color classification method 1400 is described where clinical experts classify a color space model into clinical sputum categories. Clinicians specify (S1401) a set of clinical color categories such as mucoid-clear, mucoid-frothy, mucopurulent-light white, mucopurulent-solid white, purulent-light yellow, purulent-medium yellow, purulent-dark yellow, purulent-light green, purulent-medium green, severe purulent-dark green, grey, red, brown, dark grey/black. Assuming first a clear sputum sample container background color, clinicians assign (S1402) a range of RGB numerical color features to each clinical color category where a specific clinical category is defined by a range of numerical values for each color classification such as Red (R), Green (G), and Blue (B). Next, the clinicians consider a non-clear sputum container background color and adjust (S1403) the appropriate RGB assignments to a clinical color category. For each container background color, the sputum clinical color classification categories and the assigned RGB colors are stored (S1404) for future color classification processing.

Figure 18:
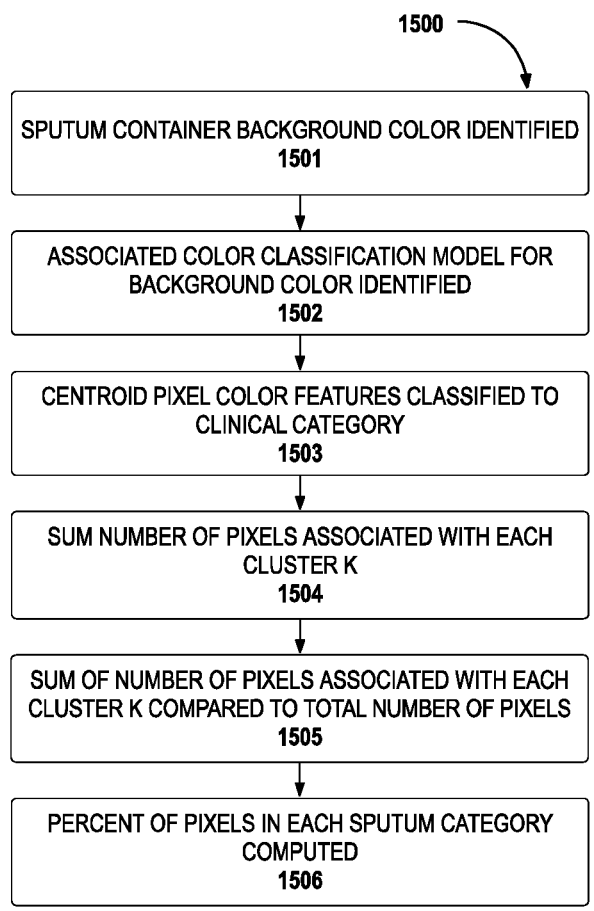
FIG. 18 is a flow chart representing a method of converting the optimal k-cluster solution into a clinical sputum classification framework.

Next, in FIG. 18 the process flow of method 1500 for converting the optimal k-cluster solution into the clinical sputum classification framework is shown. First, the algorithm identifies the sputum container background color (S1501). The associated clinical sputum color classification model for the specific background color is identified (S1502). For each cluster k, the classification algorithm identifies the centroid pixel RGB color features for the k cluster and classifies the sputum color category according to one of the following categories (S1503): as mucoid-clear, mucoid-frothy, mucopurulent-light white, mucopurulent-solid white, purulent-light yellow, purulent-medium yellow, purulent-dark yellow, purulent-light green, purulent-medium green, severe purulent-dark green, grey, red, brown, dark grey/black. Then, the number of pixels associated with each cluster k is calculated (S1504) and compared to the total number of pixels inside the sputum sample container contour (S1505). After the k clusters have been matched with a clinical sputum category, the percent of pixels in each sputum category are computed (S1506) and reported to subject 10 and/or the healthcare provider.

In other implementations, the k-means clustering algorithm can be replaced with other automated color vision clustering methods such as pillar-k means clustering, fuzzy c-means (FCM) clustering, mean-shift clustering, density-based spatial clustering, expectation-maximization clustering using gaussian mixture models, and agglomerative hierarchical clustering. It is also envisioned that multiple algorithms can be used concurrently.

In some implementations, the pixel spatial location coordinates allow for examination of the geometries within a cluster. The sum of the square deviations between the spatial coordinates of the pixels in a given cluster against the cluster's centroid are computed. Smaller values of the sum of the squared deviations represent closer location of the cluster colors in the sputum sample. Larger sum of squared deviations indicates the cluster's color category exists across the sputum sample. In some implementations, the sum of square deviations can be modified for non-linear distances between different color models and include non-linear weighted deviations between the pixels in a cluster and between the cluster's centroids.

FIG. 19 depicts an illustration of a healthcare provider report 1600 generated by the automated sputum analysis system. The patient profile 1601 and the current disease status 1602 informs the healthcare provider's interpretation of the sputum sample analysis results. The date, time, and location of the sputum sample collection are noted 1603. The sputum color categories are represented in 1604. The percent of the sputum sample pixels are reported 1605 to assist the healthcare provider in a diagnosis of an acute exacerbation and the need for antibiotic therapy.

Figure 20:
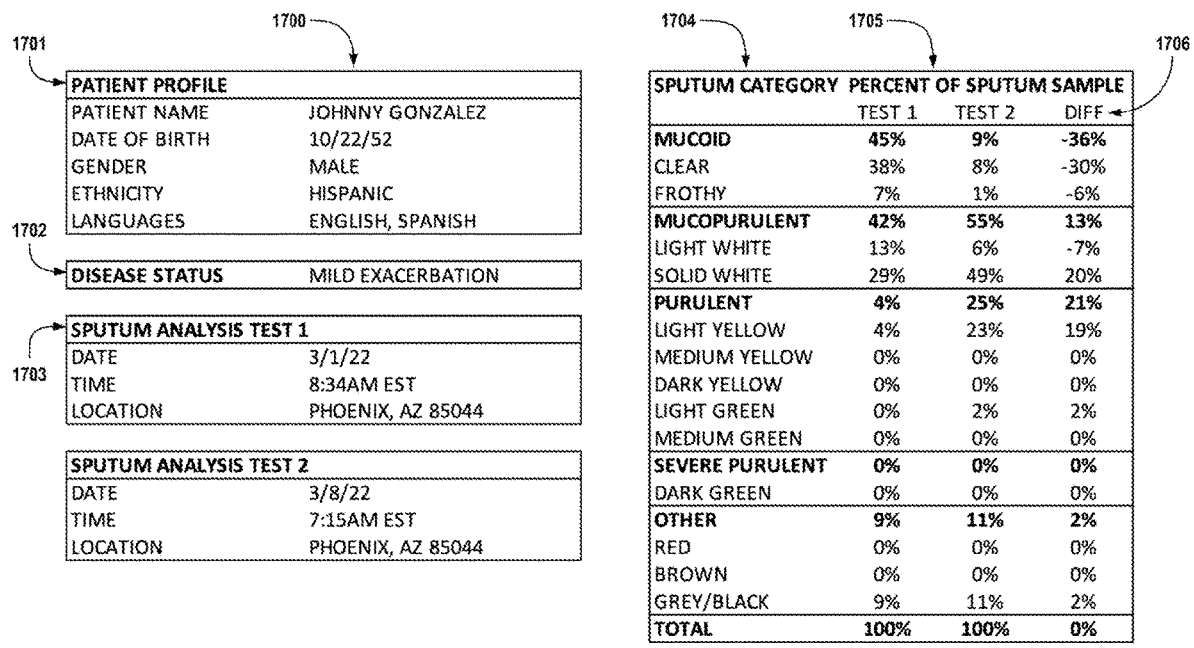
FIG. 20 depicts a healthcare provider report of the changes in sputum samples.

FIG. 20 depicts a healthcare providers report 1700 of the clinical sputum category changes in serial sputum samples. The patient profile 1701 and disease status 1702 are reported to the healthcare provider in the decision support application 106B. The date, time, and other test result data are reported 1703. The clinical sputum category 1704 and the reported sputum sample percentages 1705 are reported for each individual test. A comparative analysis of the differential between sputum analysis tests is reported 1706. In the shown embodiment, two tests are compared. In other embodiments, multiple differential measures can be illustrated to better inform the healthcare provider's decision making.

Figure 21:
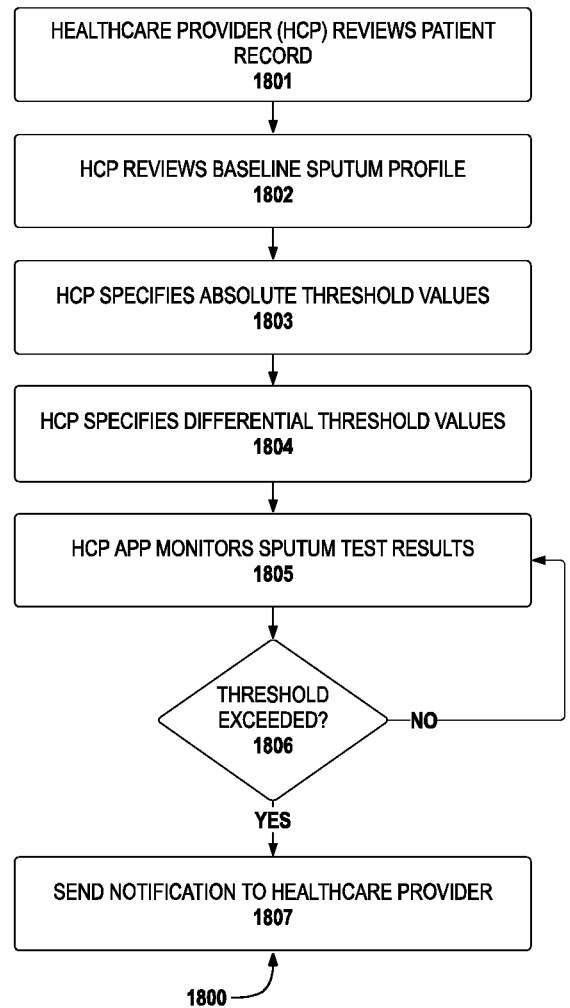
FIG. 21 is a flow chart representing a method of healthcare provider notification based on pre-specified thresholds.

FIG. 21 depicts a process flow for healthcare provider notification 1800 based on pre-specified thresholds. The healthcare provider reviews (S1801) a patient's health record in the decision support application to identify past exacerbation history and other patient diseases such as complicating co-morbidities. At the initiation of the sputum color analysis, patients are instructed through the mobile application 101B to acquire one or more sputum samples during normal respiratory conditions to create a baseline profile of a patient's sputum. The healthcare provider reviews (S1802) the baseline sputum profile before setting absolute threshold values for alert notification. The implementation allows the healthcare provider to establish (S1803) threshold values by sputum categories or by specific color categories. To monitor serial sputum analysis, the healthcare provider can establish (S1804) differential threshold values that will notify when a significant change in one or more sputum categories/colors occurs. The healthcare provider application monitors (S1805) patient's sputum test results to identify if a threshold has been exceeded (S1806) and an alert notification should be issued (S1807).

Figure 22:
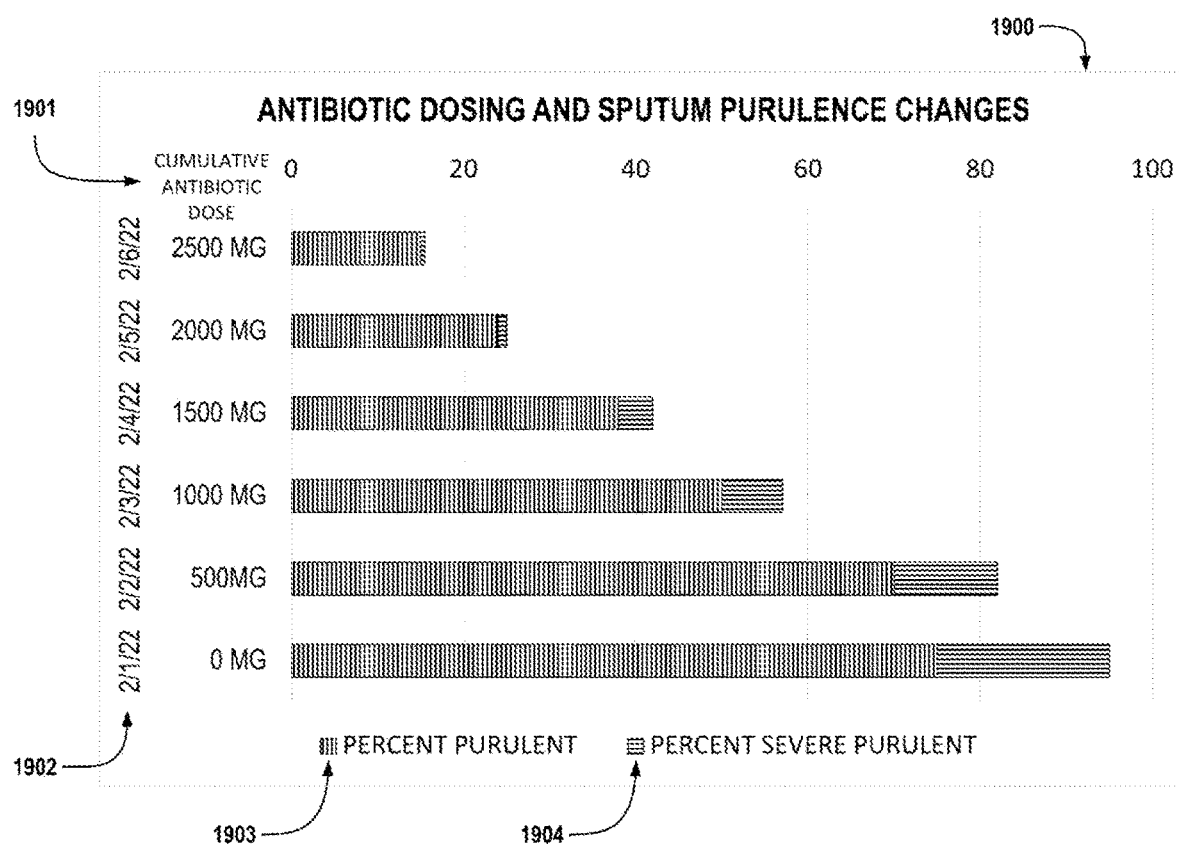
FIG. 22 depicts an illustration of the healthcare provider's decision support system to monitor changes in sputum color classification samples and antibiotic exposure over time.

FIG. 22 depicts an illustration 1900 of the healthcare provider's decision support system to monitor changes in sputum samples and antibiotic exposure 1901 over time 1902. The healthcare provider decision support system reports antibiotic exposure through patient-reported medication adherence in the mobile application 101B. Based on serial sputum samples, requested by the healthcare provider through the decision support application 106B, clinical sputum categories are reported, and the changes noted in the decision support application such as change in purulent 1903 and severe purulent 1904. This graphical representation of antibiotic dosing and sputum purulent changes provides personalized dosing regimens by monitoring a patient's therapeutic response to antibiotics.

It is important to note that the construction and arrangement of systems, methods, and devices as shown in the various examples and figures are illustrative only. Although only a few embodiments have been described in detail in this disclosure, those skilled in the art who review this disclosure will readily appreciate that many modifications are possible (e.g. variations in size, variations in cameras and light-emitting diodes, variations in dimensions, shapes and proportions of various elements, values of parameters, use of materials, orientations, etc.) without materially departing from the novel teaching and advantages of the subject matter recited. For example, elements in the edge device, lab test chamber or analysis fixture, and sputum container may be constructed of multiple parts or elements show as multiple parts may be integrally formed, the operation of the components or interfaces with smart phone and network may be reversed or otherwise varied, the length or width of the structures or connectors or other elements may be varied. The order or sequence of any process or method steps may be varied, re-sequenced, and/or performed concurrently according to alternative implementations. Other substitutions, modifications, changes, and omission may be made in the design, operating conditions, and arrangement of the various examples of embodiments without departing from the spirit or scope of this disclosure.

While this invention has been described in conjunction with the examples of the embodiments above, various alternatives, modifications, variations, improvements and/or substantial equivalents, whether known or that are or may be presently foreseen, may become apparent to those having at least ordinary skill in the art. Accordingly, the examples of embodiments of the invention, as set forth above, are intended to be illustrative, not limiting. Various changes may be made without departing from the spirit or scope of the invention. Therefore, the invention is intended to embrace known or earlier developed alternatives, modifications, variations, improvements, and/or substantial equivalents.

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . ." as used herein refers to and encompasses any and all possible combinations of one or more of the associated listed items. As an example, the phrase "at least one of A, B, C" includes A only, B only, C only, or any combination thereof (e.g., AB, AC, BC, or ABC).

For the purpose of this disclosure, the term "coupled" means the joining of two members directly or indirectly to one another. Such joining may be stationary in nature or moveable in nature. Such joining may be achieved with the two members, or the two members and any additional intermediate members being integrally formed as a single unitary body or with the two members or the two members and any additional intermediate members being attached to one another. Such joining may be permanent in nature or may be removable or releasable in nature.

The terms fixedly, non-fixedly, and removably, and variations thereof, may be used herein. The term fix, and variations thereof, refer to making firm, stable, or stationary. It should be understood, though, that fixed does not necessarily mean permanent—rather, only that a significant or abnormal amount of works needs to be used to make unfixed. The term removably, and variations thereof, refer to readily changing the location, position, and/or station. Removably is meant to be the anonym of the term fixedly. Alternatively, the term non-fixedly can be used as the antonym of fixedly.

Preferences and options for a given aspect, feature or parameter of the disclosure should, unless the context indicates otherwise, be regarded as having been disclosed in combination with any and all preferences and options for all other aspects, features, and parameters of the disclosure.

Aspects and constructions herein can be embodied in other forms without departing from the spirit or essential attributes thereof. Accordingly, reference should be made to the following claims, rather than to the foregoing specification, as indicating the scope hereof

What is claimed is:

1. A subject-controlled sputum image processing assembly for processing a bulk sputum sample expectorated from the subject into a sputum sample container, the assembly comprising:
    a tray having a receptacle to define a first location to non-fixedly receive the sputum sample container containing the bulk sputum sample expectorated from the subject into the sputum sample container;
    a device holder to define a second location and to non-fixedly receive and hold a mobile electronic device at the second location, the mobile electronic device comprising:
        a light source to illuminate the bulk sputum sample held by the sputum sample container with an illuminate light;

a light sensor to acquire a reflected light from the illuminated bulk sputum sample;

a processor; and a memory in communication with the processor, the memory including instructions executable by the processor to generate an image of the bulk sputum sample with the acquired light; and a light control enclosure removably coupled to the tray, to enclose the sputum sample container, and to help enclose the light source and the light sensor to limit a light between the light source and the light sensor, the limited light including the illuminate light emanating from the light source and the reflected light reflecting from the illuminated bulk sputum sample and substantially occluding ambient light.

2. The assembly of claim 1, further comprising a light diffuser coupled to the device holder between the light source and the bulk sputum sample, and wherein the light source includes a light-emitting diode.

3. The assembly of claim 1, wherein the mobile electronic device is a smart communication device or includes an edge device.

4. The assembly of claim 1, wherein the mobile electronic device comprises a user interface, a processor, and a memory in communication with the processor, the memory including instructions executable by the processor to provide an image processor module, a segmentation processor module, and a classification processor module.

5. The sputum image processing assembly of claim 1, further comprising a remote provider decision support in communication with the mobile electronic device, wherein the remote provider decision support includes a segmentation processor module, and a classification processor module.

6. A method of processing a bulk sputum sample from a subject contained in a sputum sample container, the method comprising:

providing the subject-controlled sputum image processing assembly of claim 1;

placing the sputum sample container in the receptacle of the tray;

placing the mobile electronic device in the device holder;

covering the sputum sample container with the light control enclosure to limit the light between the light source and the light sensor and substantially occluding ambient light;

the mobile electronic device causing the light source to illuminate the bulk sputum sample in the sputum sample container;

the mobile electronic device acquiring the light reflecting from the illuminated bulk sputum sample;

the mobile electronic device creating an image of the bulk sputum sample with the acquired light;

analyzing the sputum image to determine color information for the bulk sputum sample;

storing the sputum image for further future analyzing with a later obtained second sputum image of a second bulk sputum sample of the subject;

making a clinical sputum color classification for the bulk sputum sample; and creating a sputum report with the clinical sputum color classification.

7. The method of claim 6, further comprising diffusing the illuminated light from the light source.

8. The method of claim 6, further comprising:

instructing a subject to acquire the bulk sputum sample in the sputum sample container; and coaching the subject through processing the bulk sputum sample.

9. The method of claim 6, wherein analyzing the sputum image to determine color information comprises:

cropping the image; and segmenting the image into a plurality of pixels.

10. The method of claim 9, wherein analyzing the sputum image to determine color information further comprises:

detecting a color for each pixel of the plurality of pixels; and assigning color data to each pixel of the plurality of pixels.

11. The method of claim 10, further comprising:

clustering the plurality of pixels into a plurality of clusters;

detecting a color for each cluster of the plurality of clusters; and assigning color data to each cluster of the plurality of clusters.

12. The assembly of claim 1, further comprising a test chamber including the device holder fixed with the light control enclosure.

13. The assembly of claim 1, further comprising a test fixture including the device holder fixed with the tray.

14. A subject-controlled sputum image processing system comprising:

a sputum sample container for receiving a bulk sputum sample expectorated from the subject into the sputum sample container;

a tray having a receptacle to define a first location to non-fixedly receive the sputum sample container containing the bulk sputum sample expectorated from the subject into the sputum sample container;

a mobile electronic device comprising:

a light source to illuminate the bulk sputum sample held by the sputum sample container with an illuminate light;

a light sensor to acquire a reflected light from the illuminated bulk sputum sample;

a processor; and a memory in communication with the processor, the memory including instructions executable by the processor to generate an image of the bulk sputum sample with the acquired light; and a lab test chamber comprising an imaging tray removably receiving the mobile electronic device and an imaging hood enclosure removably coupled to the tray, to enclose the sputum sample container, and to help enclose the light source and the light sensor for limiting a light between the light source and the light sensor, the limited light including the illuminate light emanating from the light source and the reflected light reflecting from the illuminated bulk sputum sample and substantially occluding ambient light.

15. The system of claim 14, wherein the mobile electronic device is a mobile edge electronic device, and the system further comprises a mobile smart communication device in communication with the mobile edge electronic device.

16. The system of claim 15, wherein the mobile smart communication device comprises a user interface, a processor, and a memory in communication with the processor, the memory including instructions executable by the processor to lead a subject through sputum collection and analysis.

17. The system of claim 16, wherein the mobile edge electronic device further includes a segmentation processor module, and a classification processor module.

18. A subject-controlled sputum image processing system comprising:
- a sputum sample container for receiving a bulk sputum sample expectorated from the subject into the sputum sample container;
- a fixture having a stand and a receptacle to define a first location to receive the sputum sample container containing the bulk sputum sample expectorated from the subject into the sputum sample container;
- a mobile electronic device removably coupled to the stand, the mobile electronic device comprising:
  - a light source to illuminate the bulk sputum sample held by the sputum sample container with an illuminate light;
  - a light sensor to acquire a reflected light from the illuminated bulk sputum sample;
  - a processor;
  - a memory in communication with the processor, the memory including instructions executable by the processor to generate an image of the illuminated bulk sputum sample with the acquired light; and
- a lab test chamber comprising an imaging tray removably receiving the mobile electronic device and an imaging hood enclosure removably coupled to the imaging tray, to enclose the sputum sample container, and to help enclose the light source and the light sensor limiting a light between the light source and the light sensor, the limited light including the illuminate light emanating from the light source and the reflected light reflecting from the illuminated bulk sputum sample and substantially occluding ambient light.

19. The subject-controlled sputum image processing system of claim 18, wherein the mobile electronic device is a smart communication device.

20. The subject-controlled sputum image processing system of claim 18, wherein the imaging hood enclosure further encloses the mobile electronic device and the stand.

* * * * *